United States Patent [19]

Hofmann et al.

[11] 4,403,215

[45] Sep. 6, 1983

[54] APPARATUS FOR AUTOMATICALLY MONITORING BODY FUNCTIONS

[75] Inventors: Gerhard Hofmann, Freiburg; Hermann Taaks, Stegen, both of Fed. Rep. of Germany

[73] Assignee: Hellige, GmbH, Freiburg im Breisgau, Fed. Rep. of Germany

[21] Appl. No.: 255,147

[22] Filed: Apr. 17, 1981

Related U.S. Application Data

[63] Continuation of Ser. No. 864,908, Dec. 27, 1977, abandoned.

[51] Int. Cl.³ .................. G08B 23/00; A61B 5/04
[52] U.S. Cl. ..................... 340/573; 128/723; 324/65 R; 328/148; 340/657
[58] Field of Search ............ 340/870.38, 870.16, 340/870.09, 657, 661, 347 SH, 573; 324/65 R; 328/146–148, 151; 307/352, 353; 128/721, 723, 734; 364/415

[56] References Cited

U.S. PATENT DOCUMENTS

| | | |
|---|---|---|
| 3,545,429 | 12/1970 | Pelta et al. |
| 3,547,106 | 12/1970 | Bornmann ........................... 340/573 |
| 3,677,261 | 7/1972 | Day . |
| 3,727,606 | 4/1973 | Sielaff . |
| 3,802,417 | 4/1974 | Lang ................................... 340/573 |
| 3,835,840 | 9/1974 | Mount . |
| 3,875,929 | 4/1975 | Grant . |
| 3,926,177 | 12/1975 | Hardway et al. .................... 340/573 |
| 3,996,925 | 12/1976 | Djordjevich ....................... 324/65 R |
| 4,036,217 | 7/1977 | Ito et al. .............................. 128/723 |
| 4,116,231 | 9/1978 | Matsuo ............................... 128/734 |

OTHER PUBLICATIONS

"Simple Impedance Pneumograph", *Medical and Biological Engineering*, Barker et al., May, 1973, pp. 352–353.

*Primary Examiner*—James J. Groody
*Attorney, Agent, or Firm*—Robert A. Seldon; Richard Zentner

[57] ABSTRACT

A respiration monitor for use in an apnea monitor is disclosed in which a threshold value signal is automatically generated proportional to the average value of the monitored impedance of the subject during a base period selected by the operator. A comparator circuit operates to indicate respiration when the ratio between the threshold value signal and the impedance signal reaches a predetermined proportionality factor.

21 Claims, 2 Drawing Figures

APPARATUS FOR AUTOMATICALLY MONITORING BODY FUNCTIONS

This is a continuation of application Ser. No. 864,908 filed Dec. 27, 1977 now abandoned.

BACKGROUND OF THE INVENTION

1. Field of the Invention

This invention relates generally to medical apparatus for monitoring physical parameters such as respiration, blood pressure, temperature, peripheral pulse and heart rate. In particular, this invention relates to such monitors which utilize alarm or threshold circuitry utilized to indicate when the measured parameter does not reach or exceeds a preset minimum or maximum level. These limits may be related to the depth of respiration, the systolic blood pressure, the amplitude of the peripheral pressure pulse or the heart rate.

This invention particularly relates to monitors in which the limit is set proportional to the value of the parameter at a particular time, known as the base period, rather than to an absolute value. That is, during the monitoring of a particular patient, a time interval is chosen in which the operator determines that the measured parameter is considered normal or acceptable and the level is set to a value proportional to the value of the parameter monitored during this base period.

This invention finds particular usefulness in respiration monitors which are used to detect apnea, i.e., the cessation of breathing, especially for use with infants.

2. Description of the Prior Art

In respiration monitors using the impedance pneumographic technique, an electrical signal is applied to the patient, by means of electrodes, to measure the electrical impedance of the patient. It is well known that if the electrodes are properly positioned, this impedance will change as a function of respiration. A voltage signal is thereby developed, the amplitude of which is related to the depth of respiration. A comparator is used to generate a pulse whenever the voltage signal exceeds a predetermined threshold level or limit. This pulse is applied to an elapsed time measuring device which generates the apnea alarm whenever the interval between pulses exceeds a present limit.

The easiest way of providing an adjustable threshold level for use in apnea or other monitors is to utilize a manually adjustable signal source controlled, for example, by an operator-adjusted potentiometer. In this manner an alarm or threshold limit may easily be set to an absolute value, that is, independent of the monitored value of the parameter. It is often more desirable to set the threshold to a value related to the value of the parameter during the base period. That is, it may be desirable to set the threshold level so that the alarm will indicate, for example, if the body temperature rises 0.5° C. or if the amplitude of the peripheral phase drops by two-thirds or if the depth of respiration decreases by 50 percent of the base period value.

It is of particular importance to be able to set apnea alarm limits proportional to the respiration as actually monitored during the base period when using impedance pneumography because interference signals, called artifacts, unrelated to respiration may be relatively large compared to the value of the respiration related signals. Such artifacts make the immediate detection of apnea more difficult. One major cause of these artifacts is the impedance fluctuations generated by pulse waves in large blood vessels as a result of cardiac action.

In fact, clinical investigations have shown that the amplitude of the heart beat artifacts is below 40 percent of the amplitude of the signals caused by respiration if respiration is sufficient and the measuring electrodes are applied at suitable locations, namely in the eighth intercostal space in the anterior or midaxillary line.

The known method for adjusting alarm or threshold levels proportional to the monitored value of the parameter during a base period requires the operator to perform certain manual operations, as follows. The parameter signal is displayed, for example, on a cathode ray oscilloscope. When, in accordance with medical practice, the description of which is not relevant here, the operator determines that the parameter being measured is normal or acceptable, the base period is chosen. The value of the parameter is measured by manually measuring one or more signal amplitudes. The absolute value of this base period signal is calculated. The value of the threshold limit is then calculated to be a value proportional to the value of the base period signal and is applied manually to the monitor. These manual operations and calculations are cumbersome, time consuming, susceptible to error and require relatively skilled personnel.

An improved mechanism for setting an alarm or threshold level proportional to the base period value of the parameter without requiring the use of an oscilloscope is known from Hellige Apnea Monitor, Model No. 236,025.

In this device, during the time selected as the base period by the depression of a key, the operator adjusts a potentiometer to the minimum setting at which all inspirations of sufficient depth just result in the illumination of a trigger control lamp. The resultant potentiometer setting is used as the base period value of the respiration signal and the threshold limit is automatically set to a fixed proportion, i.e., 50 percent, of that value.

It is a primary object of this invention to provide apparatus for automatically and conveniently providing a threshold limit the magnitude of which has a defined relationship to the value of the monitored parameter at the time the threshold limit was set, i.e., during the time chosen as the base period.

SUMMARY OF THE INVENTION

The instant invention provides medical apparatus for monitoring physical parameters including means for automatically providing a threshold limit the mignitude of which has a defined relationship to the value of the monitored parameter during an operator-selected base period. The automatic means includes means responsive to operator control for developing a signal equal to the average or mean value of the monitored parameter during the base period and memory means for storing a limit value proportional to the mean value. The limit value may then be compared to the monitored value for generating an alarm.

This invention finds particular usefulness in a respiration monitor having an apnea alarm which includes means to develop an impedance signal voltage proportional to the changing impedance of the patient, means to develop a signal voltage related to the maximum or peak signal voltage during each cycle of impedance change, means to develop an average or arithmetic means threshold value of the peak voltage signal, means to multiply this average value signal by a preselected proportionality limit factor to develop a limit value signal, and means to generate an apnea alarm whenever the signal voltage fails to exceed the limit value signal for a predetermined minimal time interval, and means to indicate an inspiration when the ratio between the threshold value signal and the impedance signal exceeds the proportionality factor.

DETAILED DESCRIPTION OF THE PREFERRED EMBODIMENTS

Figure 1:
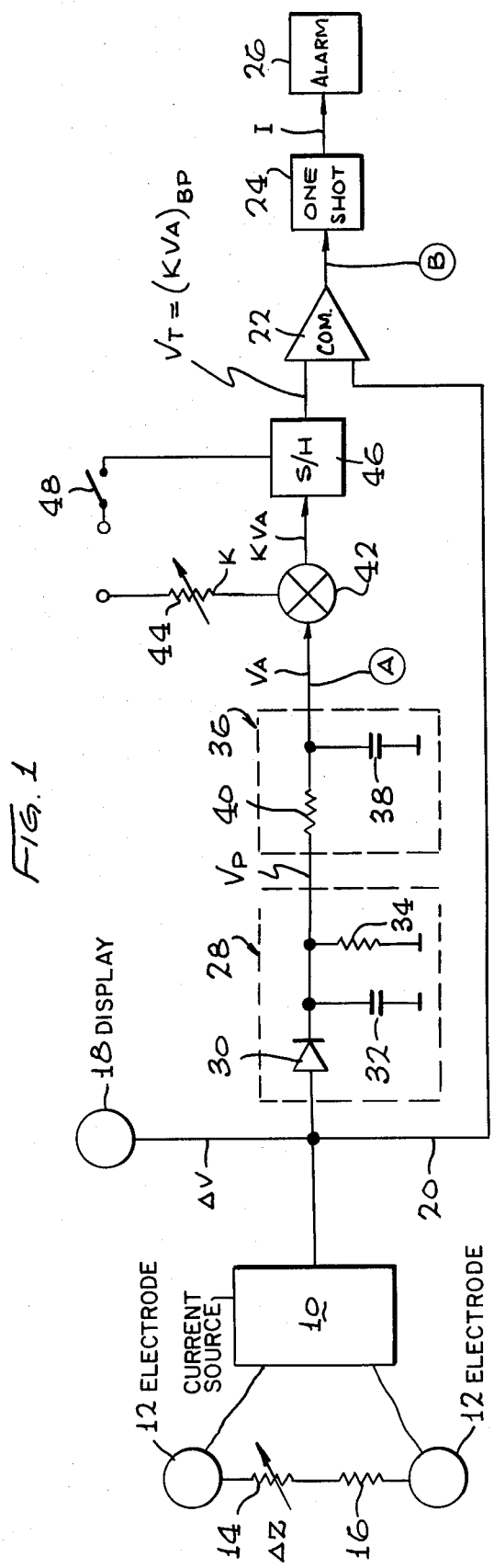
FIG. 1 is a representation of a respiration monitor having an apnea alarm including an automatic limit circuit according to the instant invention.

An apnea monitor is shown in FIG. 1, as an example of the instant invention, in which a high frequency alternating current signal is applied from current source 10 through electrodes 12 to the body of the patient, schematically represented in FIG. 1 as $\Delta Z$ or variable resistance 14. The changes in the impedance of the body between the electrodes is monitored by a signal converter such as differential amplifier 16 which measures the voltage developed across current source 10. The output signal voltage $\Delta V$ of amplifier 16 is proportional to the depth of respiration of the patient. The signal may be displayed to the equipment operator as a respiration curve by display 18 which may typically be a cathode ray oscilloscope. $\Delta V$ is also applied via line 20 to comparator 22 which generates an output pulse whenever $\Delta V$ is greater than the threshold limit $V_T$ which is applied to the other input of comparator 22. These output pulses are rated as inspirations and are applied to a timing device such as one shot 24. If such pulses are not received continuously within a preset minimum time interval, alarm circuit 26 is activated to indicate apnea.

Signal voltage $\Delta V$ is also applied to peak selector 28 which develops a voltage $V_p$ equal to the peak voltage during each inspiration. Peak selector 28 may be anyone of a number of conventional designs capable of developing a voltage proportional to the peak value of each of a series of waveforms. A convenient circuit for selector 28 is shown in FIG. 1 in which the input signal is rectified and clipped by diode 30 and then stored in capacitor 32. Resistor 34 is place in parallel with the capacitor to bleed off the signal between waveforms so that the voltage developed across capacitor 32 is dependent upon the magnitude of a single peak.

The average or arithmetic mean value $V_A$ of a series of inspiration peak voltages $V_P$ is developed by mean value circuit 36 which may conveniently be a short term memory, such as integrating capacitor 38 and resistor 40. Mean value signal $V_A$ is then applied to a programmable attenuator or multiplier such as multiplier 42 so that the limit factor K may be applied thereto. This limit factor, which for apnea alarms may conveniently be 50 percent, is preselected according to medical experience. The value for K may be locked into the circuitry by the manufacturer or infinitely adjustable by the operator. The factor may also be adjustable in steps by the operator by switches representing various observed conditions of the patient. Further, the value of the factor may be varied automatically as a result of the readings of other monitoring equipment, that is, the output of a heart rate monitor could be applied to vary the factor according to the average heart rate of the patient. The adjustable nature of the value of factor K is schematically represented in FIG. 1 by adjustable potentiometer 44.

The output of multiplier 42, $KV_A$, varies as the average value of the respiration peaks varies and is applied to sample-and-hold circuit 46 which monitors this signal and holds the current value thereof when base period key 48 is depressed to select the base period interval. The length of the base period may be varied by changing the capacitance of capacitor 38. The output of sample-and-hold circuit 46 is applied to comparator 22 and is the threshold limit value $V_T$ which is equal to the average value of the peak of the respiration signals during the base period multiplied by the limit factor K.

The apnea alarm, according to the instant invention, therefore, operates as follows. Alarm 26 is continuously inhibited as long as inspirations of a sufficient magnitude continue to occur within the time interval of the width of the pulse generated by one shot 24. The sufficiency of the inspiration is determined by comparator 22 so that any change in impedance equal to or greater than a certain factor K of the same signal during the base period generates the pulse applied to the input of comparator 22.

Various alternate constructions of the apparatus of the instant invention may be designed. Certain of these variations are described herein and may be easily understood with reference to FIG. 2 which shows in greater detail one variation of the circuitry between points A and B as shown in FIG. 1. Wherever possible, the numbering system of FIG. 1 has been retained as an aid to the reader in quickly understanding the circuitry of FIG. 2.

Figure 2:
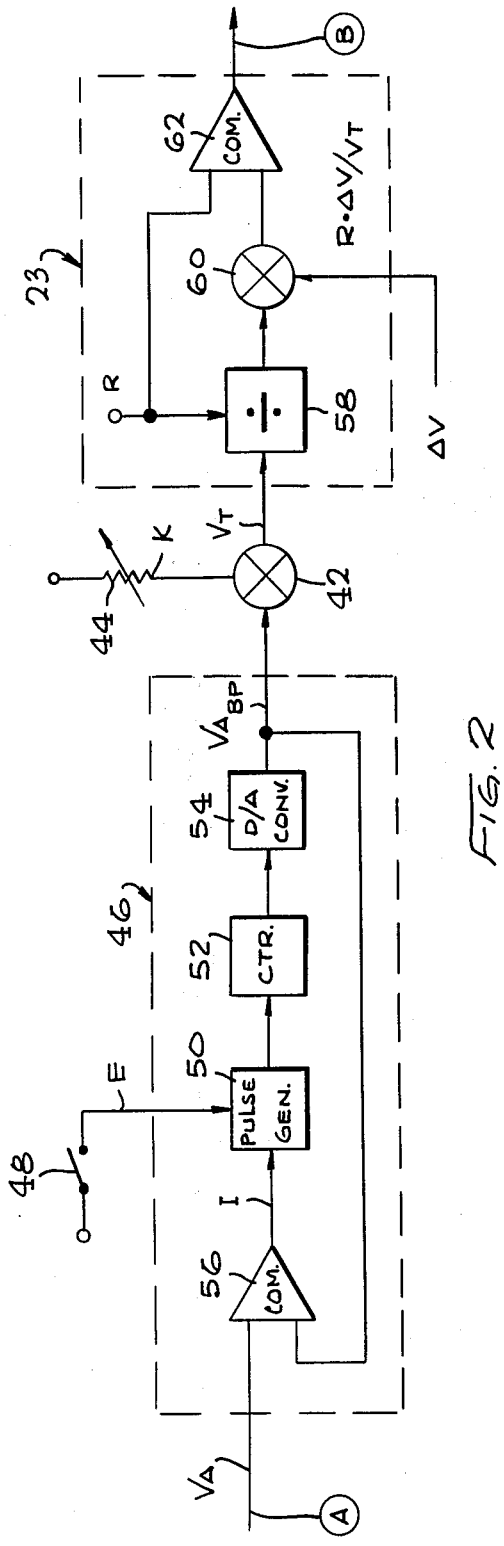
FIG. 2 is a more detailed representation of an alternate embodiment of the circuitry shown in FIG. 1 between points A and B including the sample-and-hold and comparator circuits.

One alternate to the embodiment of FIG. 1 may conveniently be accomplished by reversing the positions of multiplier 42 and sample-and-hold circuit 46 as shown in FIG. 2. In this manner, the mean value signal $V_A$ may be stored in sample-and-hold circuitry 46 before the limit factor K is applied. The output of multiplier 42 is the limit signal $V_T$ which is applied to the input of a comparator network 23. One convenient type of sample-and-hold circuit for use in the instant invention is disclosed in detail in FIG. 2 as circuit 46. The heart of this circuit is pulse generator 50. Key 48 is connected to the enable input E thereof so that generator 50 begins to generate pulses when the base period is selected. These pulses are counted in counter 52 and converted to an analog signal in digital-to-analog converter 54. When the output of converter 54 reaches the current mean value signal $V_A$, comparator 56 serves to inhibit generator 50. The resultant converter output is $V_{ABP}$, that is, the mean value signal during the base period. Converter 54 may conveniently include a memory means in its circuitry which performs the hold function of sample-and-hold circuit 46. The output of converter 54 may be applied to multiplier 42 to yield the limit value $V_T$ as discussed above.

Limit value $V_T$ is applied to comparator network 23 in the same manner as shown in FIG. 1. It may be convenient to use a comparator 62, one of whose inputs does not vary, rather than the differential comparator 22 shown in FIG. 1.

As shown in FIG. 2, the comparator network may include divider 58 to which both $V_T$ and a constant reference signal R are applied. The output of divider 58 is then multiplied in multiplier 60 by the voltage signal $\Delta V$ to yield the term $R \cdot \Delta V / V_T$. This signal is then applied to comparator 62, the other input of which is the constant reference signal R. In this arrangement, comparator 23 may be considered to be an amplifier, the input of which is $\Delta V$ and the gain of which is controlled to be inversely proportional to $V_T$. The output of comparator 62 is the pulse indicating an inspiration which is applied to one shot 24, shown in FIG. 1.

We claim:

1. A respiration indicator comprising:
    operator-actuated switch means having at least two states;
    impedance pneumograph means for determining an impedance signal related to changes in impedance of a living subject;
    threshold means responsive to the operator-actuated switch means for producing a signal indicative of the average value of the impedance signal during a base period interval; and
    comparator means for indicating an inspiration when the ratio between the threshold value signal and the impedance signal exceeds a predetermined proportionality factor.

2. The respiration indicator claimed in claim 1 wherein the base period interval is generally co-extensive with the duration of a selected one of the switch means output states.

3. The respiration indicator claimed in claim 1 further comprising:
    adaptive means responsive to changes in a physiological parameter for adapting the proportionality factor so that inspirations may be indicated during conditions of changes physiological parameters.

4. The respiration indicator claimed in claim 1, wherein the comparator means includes:
    an amplifier responsive to the impedance signal, the gain of the amplifier being inversely proportional to the threshold value signal.

5. The respirator indicator claimed in claim 1, including:
    peak detection means for storing a signal value indicative of successive peak values of the impedance signal during respiration;
    average means for producing an averaged signal indicative of the mean the peak values;
    multiplication means for producing a signal indicative of a predetermined proportion of the average signal; and
    sample and hold means responsive to a selected state of the operator-actuated switch means to sample and hold a signal proportional to the mean of the peak values,
    said comparator means for comparing the held signal with the impedance signal and for producing an output signal indicative of the relative magnitudes of the impedance signal and the predetermined proportion of the average value signal.

6. The respirator indicator of claim 5, wherein the sample and hold means is coupled between the multiplication means and the comparator means to hold the proportioned average value.

7. The respirator indicator of claim 5, wherein the sample and hold means is coupled between the averaging means and the multiplication means.

8. The respirator indicator of claim 5, wherein the sample and hold means includes:
    pulse generator means responsive to a selected output state of the switch means to produce a series of pulses,
    counter means responsive to the generation of pulses to produce an incrementally mono-directionally changing signal, and
    means for interrupting the application of pulses to the counter means when the signal therefrom is substantially equivalent to the averaged signal.

9. The respirator indicator of claim 8 including:
    comparator means coupled to the pulse generator means and responsive to the relative values of the averaged signal and counter means signal to inactivate the pulse generator means.

10. The respirator indicator of claim 1, wherein the comparator means is coupled at one input to:
    a reference value signal and is coupled at its other input to a signal representing the arithmetic product of the reference value and the ratio of the impedance signal value to said average impedance signal value.

11. The respirator indicator of claim 10 including:
    divider means responsive to a divisor signal level for receiving said average value and for producing a quotient signal level thereof,
    multiplier means responsive to the quotient signal and the impedance signal for producing a product signal thereof,
    the product and divisor signals being applied to respective inputs of the comparator means.

12. An improved respiration monitor, of the type including impedance pneumograph means for generating an impedance signal related to changes in impedance of a living subject, means for displaying the impedance signal, and a comparator responsive to the impedance signal and a threshold limit signal for generating an output indicative of respiration, wherein the improvement comprises:
    automatic threshold limit generating means responsive to the impedance signal for generating the threshold limit signal proportional to an average value of the impedance signal during a selected base period interval; and
    means for altering at least one of the signals applied to the comparator by a selected proportionality factor.

13. The improved respiration monitor of claim 12, wherein the comparator includes:
    an amplifier responsive to the impedance signal, the gain of the amplifier being inversely proportional to the threshold limit.

14. The improved respiration monitor of claim 12, wherein the improvement further comprises:
    an apnea alarm circuit responsive to the comparator output for indicating the cessation of respiration.

15. The improved respiration monitor of claim 1, wherein the signal altering means includes:
    means responsive to a monitored physiological parameter for adapting the selected proportionality factor in response to changes in the monitored physiological parameter.

16. The improved respiration monitor of claim 12, wherein the automatic threshold limit generating means includes:
    means for generating a signal related to the average peak value of impedance changes; and
    means for storing a manually selected current value of the generated signal.

17. The improved respiration monitor of claim 16, wherein the storing means includes:
   a pulse generator;
   means for manually enabling the pulse generator;
   a pulse counter responsive to the pulse generator;
   a digital to analog converter responsive to the pulse counter for generating an input to the storing means; and
   a comparator responsive to a current output of the storing means and the output of the average peak value generating means for disabling the pulse generator when the output of the storing means is equal to the output of the peak value generating means.

18. The improved respiration monitor of claim 16, wherein the automatic threshold limit generating means includes:
   means for manually setting a ratio between the average peak value of the impedance signal changes and the output of the storing means to a selected proportionality factor to form a threshold level signal.

19. The improved respiration monitor of claim 16, wherein the improvement further comprises:
   means for selecting the base time period interval by selecting the average peak value signal to be stored in the storing means.

20. The improved respiration monitor as defined in claim 18 further comprising wherein the comparator includes:
   a comparator network having as components
      a fixed-value reference signal associated with the comparator network;
      a divider circuit for dividing the fixed-value reference signal by the threshold level signal to form a divider output signal;
      a multiplier for multiplying the divider output signal by an impedance signal to provide a proportioned impedance signal; and
      a comparator, responsive to the fixed reference signal and the proportioned impedance signal, for providing an inspiration indication when the proportioned signal exceeds the fixed reference signal.

21. The improved respiration monitor as defined in claim 20 wherein :
   the comparator network forms a variable gain amplifier having a gain that is inversely proportional to the level of the threshold level signal.

* * * * *